(12) United States Patent
Uchiyama

(10) Patent No.: US 8,358,137 B2
(45) Date of Patent: Jan. 22, 2013

(54) METHOD AND APPARATUS FOR EXAMINING ION-CONDUCTIVE ELECTROLYTE MEMBRANE

(75) Inventor: Naoki Uchiyama, Hamamatsu (JP)

(73) Assignee: Kabushiki Kaisha Atsumitec, Shizuoka (JP)

(*) Notice: Subject to any disclaimer, the term of this patent is extended or adjusted under 35 U.S.C. 154(b) by 247 days.

(21) Appl. No.: 12/668,635

(22) PCT Filed: Jul. 3, 2008

(86) PCT No.: PCT/JP2008/062097
§ 371 (c)(1),
(2), (4) Date: Jan. 11, 2010

(87) PCT Pub. No.: WO2009/008335
PCT Pub. Date: Jan. 15, 2009

(65) Prior Publication Data
US 2010/0206455 A1    Aug. 19, 2010

(30) Foreign Application Priority Data
Jul. 9, 2007    (JP) .................................. 2007-179607

(51) Int. Cl.
*G01N 27/62*    (2006.01)
(52) U.S. Cl. ............. 324/464; 324/459; 324/705; 73/45; 702/35
(58) Field of Classification Search .................. 324/432, 324/718, 456; 702/35; 73/45; 204/520, 204/518, 415, 400, 416, 640, 627; 429/482, 429/483, 400; 156/164
See application file for complete search history.

(56) References Cited

U.S. PATENT DOCUMENTS

| | | | |
|---|---|---|---|
| 2003/0170520 A1* | 9/2003 | Fujii et al. | ......................... 429/32 |
| 2004/0197633 A1* | 10/2004 | Yamamoto et al. | ............. 429/34 |
| 2009/0108856 A1* | 4/2009 | Yonushonis et al. | ........... 324/718 |

FOREIGN PATENT DOCUMENTS

| | | |
|---|---|---|
| JP | 2001-23665 | 1/2001 |
| JP | 2004-214089 | 7/2004 |
| JP | 2004-233097 | 8/2004 |
| JP | 2005-201822 | 7/2005 |
| JP | 2006-286397 | 10/2006 |
| JP | 2007-311191 | 11/2007 |
| JP | 2007-311193 | 11/2007 |

* cited by examiner

*Primary Examiner* — Jermele M Hollington
*Assistant Examiner* — Alesa Allgood
(74) *Attorney, Agent, or Firm* — Cozen O'Connor

(57) ABSTRACT

A detection membrane is joined to a first surface of an electrolyte membrane. After the detection membrane is hydrogenated, oxygen is supplied to a space facing a second surface of the electrolyte membrane. If the electrolyte membrane has a defect, oxygen leaks to the first surface, resulting in a change in resistance of the detection membrane owing to dehydrogenation of the detection membrane. The defect is recognized by this change. An air electrode is joined to the second surface, and an electric circuit is connected between the detection membrane and the air electrode. After hydrogenating the detection membrane and ionizing oxygen supplied to a space facing the air electrode, oxygen ions permeate through the electrolyte membrane and dehydrogenate the detection membrane. Uniformity of the oxygen ion conductivity is examined by measuring resistance of the detection membrane, which varies depending on the amount of oxygen ions, for each region.

13 Claims, 7 Drawing Sheets

METHOD AND APPARATUS FOR EXAMINING ION-CONDUCTIVE ELECTROLYTE MEMBRANE

RELATED APPLICATIONS

This is a U.S. National Phase Application under 35 USC §371 of International Application PCT/JP2008/062097 filed on Jul. 3, 2008.

This application claims the priority of Japanese Patent Application No. 2007-179607 filed Jul. 9, 2007, the entire content of which is hereby incorporated by reference.

TECHNICAL FIELD

The present invention relates to a method and apparatus for examining an ion-conductive electrolyte membrane.

BACKGROUND ART

An ion-conductive electrolyte membrane (hereinafter, sometimes referred to simply as "electrolyte membrane") is used in a fuel cell, for example, and an oxygen ion-conducive electrolyte membrane is used in a membrane electrode assembly of a solid oxide fuel cell, for example. Such membrane electrode assembly is constructed by joining a fuel electrode (hydrogen electrode) to one side of a solid oxide electrolyte membrane which is an electrolyte membrane, and an air electrode (oxygen electrode) to the other side. In the solid oxide fuel cell having such membrane electrode assembly, hydrogen or carbon monoxide is supplied to the fuel electrode while oxygen or air is supplied to the air electrode. With the membrane electrode assembly heated, oxygen gains electrons at the air electrode to form oxygen ions. The oxygen ions permeate through the electrolyte membrane to reach the fuel electrode, and react with hydrogen (or carbon monoxide) to form water (water vapor) or carbon dioxide and release electrons. The electrons travel through a load, thus supply electric power to the load, and when the electrons reach the air electrode, the electrons ionize oxygen supplied to the air electrode.

In such solid oxide fuel cell, if the electrolyte membrane constituting part of the membrane electrode assembly has a defect, such as a pin hole or a crack, gas leaks through the electrolyte membrane, resulting in a reduction in electric power generation capacity. If, for example hydrogen gas is supplied to a space facing one side of the electrolyte membrane, such defect allows the hydrogen gas to leak through it to the other side of the electrolyte membrane. Thus, the presence of a defect can be detected by measuring the concentration of leaked hydrogen gas with a hydrogen sensor. The hydrogen sensor for use in such measurement can be formed using a hydrogen storing alloy, for example, as disclosed in Unexamined Japanese Patent Publication No. 2004-233097, for example.

In a solid oxide fuel cell having a plurality of membrane electrode assemblies electrically connected in series to increase output voltage, maximum output current is determined by the membrane electrode assembly lowest in oxygen ion conductivity. It is therefore desirable that the membrane electrode assemblies connected in series be as uniform in oxygen ion conductivity as possible. Thus, a technique of estimating the oxygen ion conductivity of an electrolyte membrane by attaching a metal electrode to either side of the electrolyte membrane and measuring an electrical characteristic of the electrolyte membrane, such as AC impedance, has been developed, as proposed in Unexamined Japanese Patent Publication No. 2006-286397, for example.

In the examination method by detecting leaked hydrogen gas diffused in an atmosphere, an ability for detecting a defect of the electrolyte membrane lowers due to the diffusion of leaked hydrogen gas. In addition, detection of leaked hydrogen gas in an atmosphere does not give the location of the defect.

The measurement of an electrical characteristic (AC impedance or the like) of an electrolyte membrane is not direct measurement of oxygen ion conductivity; it only gives an estimate of oxygen ion conductivity. In addition, whether or not the electrolyte membrane has uniform oxygen ion conductivity in every region cannot be examined by this measurement.

DISCLOSURE OF THE INVENTION

The present invention has been made in view of the problems as mentioned above. The primary object of the present invention is to provide an examination method and apparatus capable of more accurately examining an ion-conductive electrolyte membrane.

In order to achieve the above object, in a method for examining an ion-conductive electrolyte membrane according to the present invention, a detection membrane including a thin film layer is joined to a first surface of the ion-conductive electrolyte membrane, and hydrogen gas is supplied to a space facing the first surface of the ion-conductive electrolyte membrane to hydrogenate the detection membrane. Thereafter, oxygen gas is supplied to a space facing a second surface of the ion-conductive electrolyte membrane. If the ion-conductive electrolyte membrane has a defect, oxygen gas leaks from the second surface to the first surface of the ion-conductive electrolyte membrane through the defect, so that the thin film layer is dehydrogenated in a portion near the defect and varies in electric resistance. Thus, whether or not a defect exists can be examined quickly with high accuracy by observing a change in electric resistance of the thin film layer which results from the dehydrogenation.

If, for example, the thin film layer of the detection membrane is provided for each of a plurality of regions into which a surface of the ion-conductive electrolyte membrane is divided, the thin film layer corresponding to a region having a defect is dehydrogenated by leaked oxygen gas and varies in electric resistance. Thus, in this case, the region having a defect can be identified by measuring the electric resistance of each of the thin film layers provided for the respective regions to detect a thin film layer having undergone a change in electric resistance.

Gas pressure in the space facing the second surface of the ion-conductive electrolyte membrane may be kept higher than gas pressure in the space facing the detection membrane. In this case, an increased amount of oxygen gas leaks through a defect, enabling quicker detection of the defect.

The detection membrane may include, in addition to the thin film layer, a catalyst layer which is brought in contact with the ion-conductive electrolyte membrane, for example. In this case, the thin film layer varies in electric resistance by undergoing dehydrogenation by oxygen gas passing through the ion-conductive electrolyte membrane, under the catalytic action of the catalyst layer in contact with the ion-conductive electrolyte membrane. A defect can be found out by detecting such change in electric resistance.

Specifically, the thin film layer may be formed of a magnesium-nickel alloy, a magnesium-titanium alloy, a magnesium-niobium alloy, a magnesium-manganese alloy, a magnesium-cobalt alloy or magnesium, for example. The catalyst layer may be formed of palladium or platinum, for example. In this case, the thin film layer varies in electric resistance by hydrogenation or dehydrogenation, quickly and reversibly.

In order to achieve the above object, in another method for examining an ion-conductive electrolyte membrane according to the present invention, a first surface of the ion-conductive electrolyte membrane is divided into a plurality of regions. A detection membrane having thin film layers provided to correspond to those regions, respectively, is joined to the first surface of the ion-conductive electrolyte membrane, while an air electrode is joined to a second surface of the ion-conductive electrolyte membrane. Hydrogen gas is supplied to a space facing the detection membrane to hydrogenate the detection membrane. In this state, an electric circuit is connected between the thin film layers and the hydrogen electrode for each of the regions, and the ion-conductive electrolyte membrane is heated to have oxygen ion conductivity. When, in this state, oxygen gas is supplied to a space facing the air electrode, the oxygen gas is ionized at the air electrode. The oxygen ions formed are supplied from the air electrode to the ion-conductive electrolyte membrane, permeate through the ion-conductive electrolyte membrane and dehydrogenate the thin film layers. The dehydrogenated thin film layers each vary in electric resistance to a degree depending on the amount of the oxygen ions permeating through the corresponding region of the ion-conductive electrolyte membrane.

Suppose that all the regions are equal in area and shape and that the catalyst layer as well as the thin film layers are uniform in chemical and electrical characteristics for all the regions. If the oxygen ion conductivity of the ion-conductive electrolyte membrane is uniform in all the regions, all the thin film layers corresponding to the respective regions uniformly vary in electric resistance. Thus, by measuring the electric resistance of each of the thin film layers provided for the respective regions in the manner described above and examining whether or not the thin film layers have undergone a uniform change in electric resistance, it can be quickly determined whether or not the ion-conductive electrolyte membrane has uniform oxygen ion conductivity.

This makes it possible to quickly sort out the ion-conductive electrolyte membranes or membrane electrode assemblies having uniform oxygen ion conductivity. Application of such examination method to a fuel cell manufacturing process, for example, can simplify the manufacturing process and reduce the cost.

The electric circuit may be a power supply circuit, where a negative terminal of the power supply circuit is electrically connected to the air electrode, and a positive terminal of the power supply circuit is electrically connected to the thin film layers, for example. In this case, electrons are supplied to the air electrode to promote the ionization of oxygen gas at the air electrode. Further, electrical repulsive force generated by a negative potential applied by the negative terminal helps the oxygen ions permeate through the ion-conductive electrolyte membrane to reach the detection membrane. In other words, the electrical repulsive force increases the oxygen ion conductivity of the ion-conductive electrolyte membrane, enabling better examination of the ion-conductive electrolyte membrane on uniformity of oxygen ion conductivity.

The detection membrane may include, in addition to the thin film layers, a catalyst layer which is brought in contact with the ion-conductive electrolyte membrane, for example. In this case, the thin film layers vary in electric resistance by undergoing dehydrogenation by oxygen ions permeating through the ion-conductive electrolyte membrane, under the catalytic action of the catalyst layer. Thus, whether or not the ion-conductive electrolyte membrane has uniform oxygen ion conductivity can be examined by detecting the electric resistance of the thin film layer in each region.

The air electrode may include an oxygen diffusion membrane and a cathode, where the cathode is electrically connected to the negative terminal of the power supply circuit and brought in contact with the ion-conductive electrolyte membrane, for example. In this case, the oxygen diffusion membrane diffuses oxygen gas, resulting in efficient production of oxygen ions at the cathode.

Specifically, the thin film layers may be each formed of a magnesium-nickel alloy, a magnesium-titanium alloy, a magnesium-niobium alloy, a magnesium-manganese alloy, a magnesium-cobalt alloy or magnesium, for example. The catalyst layer, on the other hand, may be formed of palladium or platinum, for example. In this case, the thin film layers vary in electric resistance by hydrogenation or dehydrogenation, quickly and reversibly.

In order to achieve the above-mentioned object, an apparatus for examining an ion-conductive electrolyte membrane according to the present invention comprises a detection membrane having a plurality of thin film layers and joined to a first surface of the ion-conductive electrolyte membrane, and an air electrode joined to a second surface of the ion-conductive electrolyte membrane, wherein the apparatus further comprises a container providing a space facing the air electrode and a space facing the detection membrane, an electric circuit selectively connected between the air electrode and each of the thin film layers arranged to correspond to a plurality of regions into which the first surface of the ion-conductive electrolyte membrane is divided, with a switch interposed, a heater heating the ion-conductive electrolyte membrane, thereby causing the ion-conductive electrolyte membrane to have oxygen ion conductivity, and an ohmmeter measuring electric resistance of each of the thin film layers.

In this examination apparatus, hydrogen gas is supplied to the space facing the detection membrane to hydrogenate the detection membrane. Thereafter, with the switch in "OFF" position, oxygen gas is supplied to the space facing the air electrode, and electric resistance of each of the thin film layers is measured by the ohmmeter. If the ion-conductive electrolyte membrane has a defect, the thin film layer corresponding to the region with the defect is dehydrogenated and varies in electric resistance. Thus, whether or not a defect exists can be examined by observing a change in electric resistance of each thin film layer.

Further, the ion-conductive electrolyte membrane is heated by the heater to have oxygen ion conductivity, and with the switch in "ON" position, oxygen gas is supplied to the space facing the air electrode. The ohmmeter measures electric resistance of each of thin film layers connected to the electric circuit. Here, by examining whether or not the electric resistance detected for each of the thin film layers are uniform, it can be examined whether or not the ion-conductive electrolyte membrane has uniform oxygen ion conductivity.

Thus, this examination apparatus allows both the examination of the ion-conductive electrolyte membrane for defects and the examination of the ion-conductive electrolyte membrane on uniformity of oxygen ion conductivity to be conducted in a continuous process only by operations such as hydrogenating the detection membrane, operating the switch, operating the heater and supplying hydrogen gas. This makes it possible to conduct examination and sort out the ion-conductive electrolyte membranes or membrane electrode assemblies having no defect and being uniform in oxygen ion conductivity, at reduced costs.

The electric circuit may be a power supply circuit, where a negative terminal of the power supply circuit is electrically connected to the air electrode, and a positive terminal of the power supply circuit is electrically connected to the thin film layers. In this case, electrons are supplied to the air electrode to promote the ionization of oxygen at the air electrode. Further, electrical repulsive force generated by a negative potential applied by the negative terminal helps the oxygen ions permeate through the ion-conductive electrolyte membrane to reach the detection membrane. In other words, the electrical repulsive force increases the oxygen ion conductivity of the ion-conductive electrolyte membrane, enabling better examination of the ion-conductive electrolyte membrane on uniformity of oxygen ion conductivity.

The apparatus may further comprise a gas pressure regulation means for keeping gas pressure in the space facing the air electrode higher than gas pressure in a space facing the detection membrane. In this case, an increased amount of oxygen gas leaks through a defect, enabling quicker detection of the defect.

BEST MODE OF CARRYING OUT THE INVENTION

Figure 1:
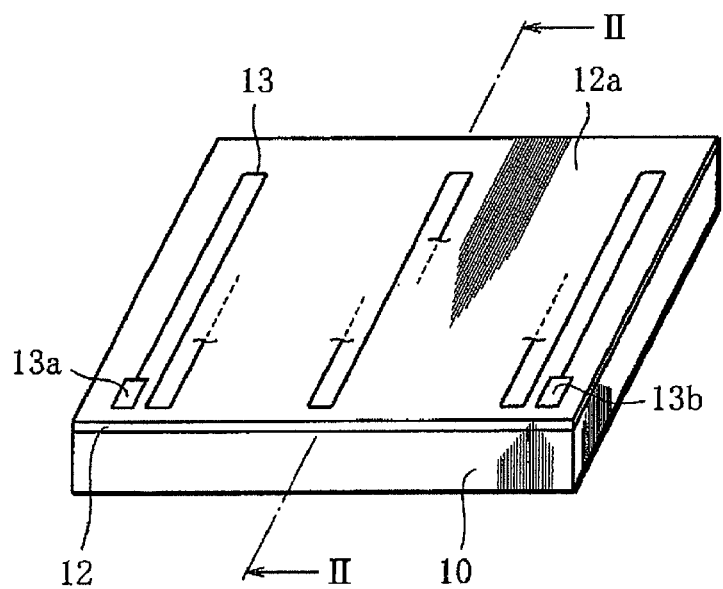
FIG. 1 is a perspective view showing an electrolyte membrane to be examined by an examination method according to a first embodiment of the present invention, and a detection membrane joined to the electrolyte membrane.

Referring to the drawings, methods and apparatuses for examining an ion-conductive electrolyte membrane according to embodiments of the present invention will be described in detail.

First, as a method for examining an ion-conductive electrolyte membrane according to a first embodiment of the present invention, a method for examining whether or not an ion-conductive electrolyte membrane has a defect, such as a pin hole or a crack, will be described with reference to FIGS. 1 to 3.

FIG. 1 is a perspective view showing an electrolyte membrane to be examined and a detection membrane joined to the electrolyte membrane. FIG. 2 is a cross-sectional view of the electrolyte membrane, etc. taken along line II-II in FIG. 1, and FIG. 3 is a schematic diagram showing an example of how the electrolyte membrane, etc. shown in FIG. 1 are arranged in a container to conduct examination.

Figure 2:
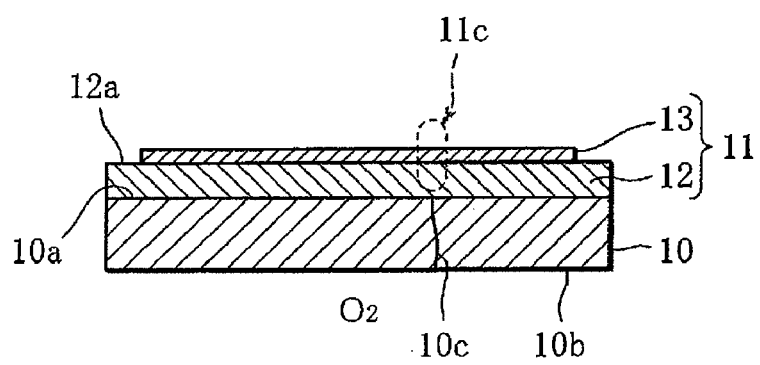
FIG. 2 is a schematic cross-sectional view taken along line II-II in FIG. 1.

As shown in FIGS. 1 and 2, a detection membrane 11, equal in planar shape to an electrolyte membrane 10, comprises a catalyst layer 12 and a thin film layer 13. The catalyst layer 12 is joined to a first surface 10a constituting one side of the electrolyte membrane 10, and the thin film layer 13 is formed on the surface of the catalyst layer 12. As shown in FIG. 1, the thin film layer 13 is in the shape of a line that extends meandering almost all over the surface 12a of the catalyst layer 12. An electrode 13a is formed at an end of the thin film layer 13, while an electrode 13b is formed at the other end thereof. Reference character 10b in FIG. 2 denotes a second surface constituting the other side of the electrolyte membrane 10. The electrolyte membrane 10 may be formed of 8 mol-YSZ (yttria stabilized zirconia), 5 mol-YSZ, SDC (scandia doped ceria), GDC (gadolinium doped ceria), ScSZ (scandia stabilized zirconia) or the like, for example.

The thin film layer 13 is a thin film of elemental composition MgNi$x$ ($0 \leqq x < 0.6$), for example. Alternatively, the thin film layer 13 may be formed of a magnesium-titanium alloy, a magnesium-niobium alloy, a magnesium-manganese alloy, a magnesium-cobalt alloy or magnesium. The catalyst layer 12 is formed of palladium or platinum, for example, and 1 nm to 100 nm thick. When the detection membrane 11 described above is exposed to an atmosphere with a hydrogen concentration of about 100 ppm or more, the thin film layer 13 is quickly and reversibly hydrogenated, in ten ms or so, and thus quickly varies (increases) in electric resistance (hereinafter, sometimes referred to simply as "resistance").

When oxygen molecules are supplied to the hydrogenated thin film layer 13, the oxygen molecules combine with hydrogen molecules that have hydrogenated the thin film layer 13 to form water vapor, or in other words, dehydrogenate the thin film layer 13. When exposed to an atmosphere with an oxygen concentration of about 100 ppm or more, the thin film layer 13 is dehydrogenated in ten ms or so, and thus quickly varies (reduces) in resistance.

Incidentally, if a thin film layer 13 and a catalyst layer 12 are formed on a polyethylene sheet in this order to form a detection membrane 11, it is easy to handle. In this case, the polyethylene sheet is on the top surface of the detection membrane 11 shown in FIGS. 1 and 2.

Figure 3:
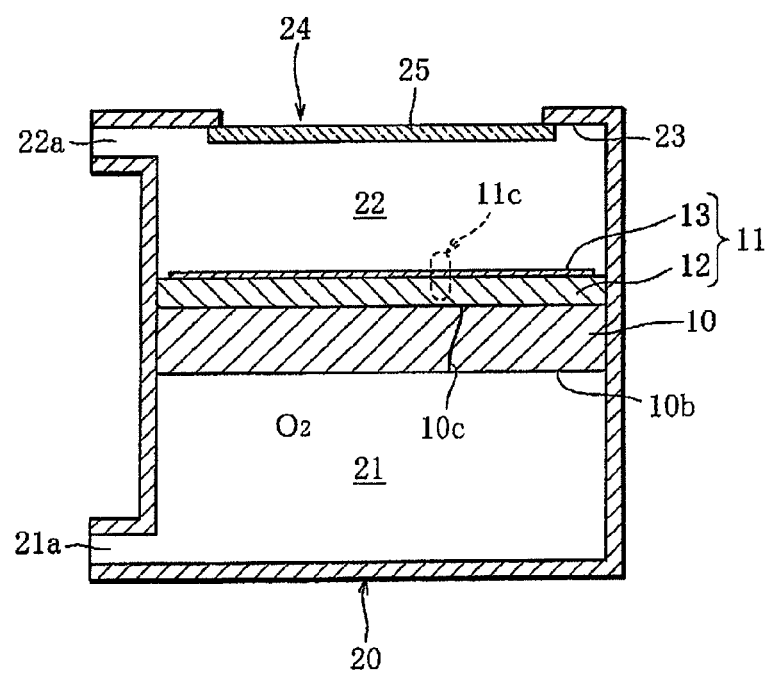
FIG. 3 is a diagram showing an example of how an electrolyte membrane, etc. are arranged in a container in order to examine the electrolyte membrane for defects, by the examination method according to the first embodiment of the present invention.

In examination of the electrolyte membrane 10, the electrolyte membrane 10 with the detection membrane 11 joined is arranged in a container 20 as shown in FIG. 3. Then, first, hydrogen gas ($H_2$) is supplied to a second space 22, through a second supply port 22a of the container 20, by a pump (not shown), for example, to hydrogenate the thin film layer 13 of the detection membrane 11, under the catalytic action of the catalyst layer 12. After the thin film layer 13 is hydrogenated this way, inert gas such as nitrogen, argon or helium, for example, is supplied to the second space 22 by a pump (not shown), for example. Such gas is supplied in order to keep the thin film layer 13 in the hydrogenated state. Alternatively, while supplying inert gas to the second space 22, a slight amount of hydrogen may be supplied to create a hydrogen concentration of 100 ppm to 1% or so, for example, in the second space 22 to hydrogenate the detection membrane 11. Then, oxygen gas ($O_2$) is supplied to a first space 21 facing the second surface 10b of the electrolyte membrane 10, through a first supply port 21a. The first space 21 and the second space 22 are separated by the electrolyte membrane 10. It is preferable to keep the gas pressure in the first space 21 higher than the gas pressure in the second space 22. Incidentally, a window 24 is provided in a wall 23 surrounding the second space 22 to allow transfer of the electrolyte membrane 10 into and from the container 20, etc. The window 24 is closed with a glass panel 25. The electrolyte membrane 10 with the detection membrane 11 joined is fixed in place inside the container 20, by means of a frame (not shown) surrounding it, for example.

When the electrolyte membrane 10 does not have a defect such as a pin hole, oxygen gas supplied to the first space 21 is prevented from contacting the detection membrane 11 by the electrolyte membrane 10. Consequently, the detection membrane 11 is not dehydrogenated, so that the resistance between the electrodes 13a and 13b of the thin film layer 13 (hereinafter, sometimes referred to as "resistance of the thin film layer 13") does not vary.

When the electrolyte membrane 10 has a crack 10c (defect), on the other hand, oxygen gas leaks from the second surface 10b side to the first surface 10a side of the electrolyte membrane 10 through the crack 10c. Consequently, the thin film layer 13 is dehydrogenated in a region 11c of the detection membrane 11 near the crack 10c, to a degree depending on the amount of leaked oxygen gas, resulting in a quick change in resistance of the thin film layer 13. Even if the crack 10c is not right under the thin film layer 13, leaked oxygen gas diffuses near the crack 10c and causes a change in resistance in some portion of the thin film layer 13 extending almost all over the surface 12a of the catalyst layer 12. In other words, if the value of resistance of the thin film layer 13 after the supply of oxygen gas to the first space 21 is different from that before the supply, it can be inferred that the thin film layer 13 has been dehydrogenated by the oxygen gas that has leaked owing to a defect of the electrolyte membrane 10, and therefore it can be determined that the electrolyte membrane 10 has a defect such as a pin hole.

The joining of the detection membrane 11 to the first surface 10a of the electrolyte membrane 10 does not need to create a perfectly tight contact leaving no space between them at all. The reason is that even if both membranes are joined together with a slight space between them, oxygen gas leaking through the crack 10c can dehydrogenate the thin film layer 13 in a portion nearest to the crack 10c.

In examination of an oxygen ion-conductive electrolyte membrane, the electrolyte membrane 10 may have an oxygen electrode joined to the second surface 10b. The reason is that if the electrolyte membrane 10 has a defect, oxygen gas permeates through the oxygen electrode, then leaks through the defect to the first surface 10a of the electrolyte membrane 10 and dehydrogenates the thin film layer. Thus, a semifinished electrode membrane assembly with an oxygen electrode joined to an oxygen ion-conductive electrolyte membrane can be examined for defects. Further, the oxygen electrode joined adds its thickness to the assembly consisting of the detection membrane 11 and the electrolyte membrane 10 joined together (the membranes are each very thin), thereby making the electrolyte membrane 10, etc. easy to handle.

The shape of the electrolyte membrane is not restricted to a flat plate as in the present embodiment; It may be in another planar shape. If the electrolyte membrane is in the shape of a tube, the examination may be conducted by joining a detection membrane onto the outer cylindrical surface of the tubular electrolyte membrane and supplying oxygen gas to the space inside the tube, for example.

Figure 5:
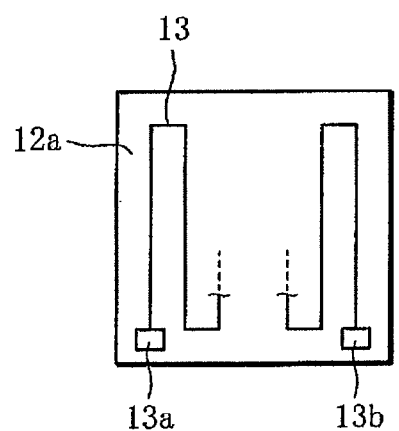
FIG. 5 is a plan view showing a schematic arrangement of a thin film layer, etc. for one region of the electrolyte membrane of FIG. 4.
Figure 6:
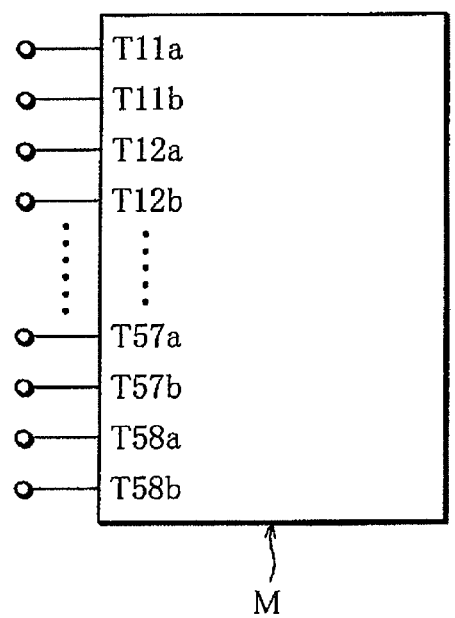
FIG. 6 is a diagram showing an example of an ohmmeter for measuring resistance of thin film layers arranged to correspond to the respective regions of the electrolyte membrane of FIG. 4.

Next, as a method for examining an ion-conductive electrolyte membrane according to a second embodiment of the present invention, a method for identifying a portion of an ion-conductive electrolyte membrane having a defect will be described with reference to FIGS. 4 to 6. The components similar in function to those in the first embodiment will be assigned the same reference characters and the description thereof will be omitted.

Figure 4:
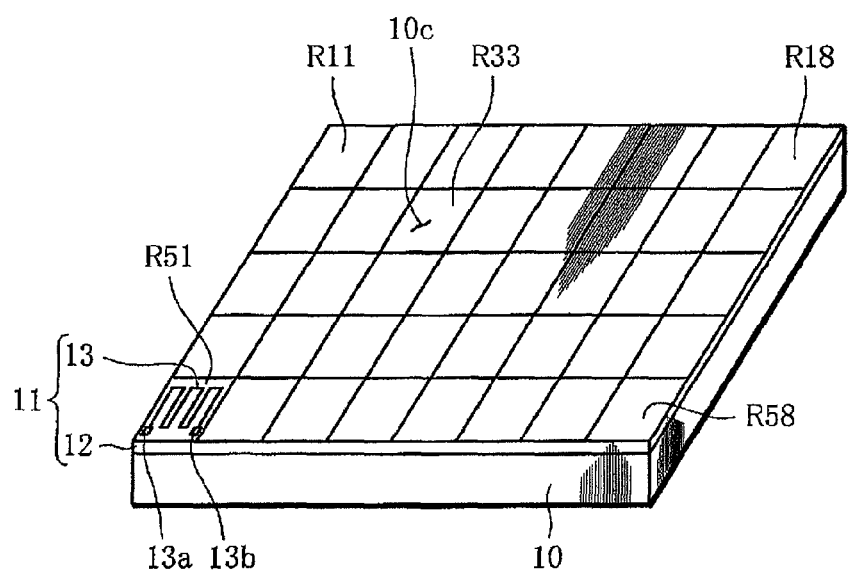
FIG. 4 is a perspective view showing an electrolyte membrane to be examined by an examination method according to a second embodiment of the present invention, and a detection membrane joined to the electrolyte membrane.

As shown in FIG. 4, a first surface 10a constituting one side of an electrolyte membrane 10 is divided laterally into 8 and vertically into 5, thus into 40 regions (equal square regions). For each of surface regions (regions R11 to R58) of a detection membrane 11 corresponding to these regions, a thin film layer 13 is formed with electrodes 13a and 13b, as shown in FIG. 5.

The thin film layers 13 in the respective regions are equal in elemental composition, shape, etc., and therefore uniform in chemical and electrical characteristics. The thin film layers 13 in the regions R11 to R58 are electrically connected to an ohmmeter M shown in FIG. 6. The ohmmeter M has terminals 11a to 58a and terminals 11b to 58b, corresponding to the regions R11 to R58. The terminals 11a and 11b form a pair and are electrically connected to the electrodes 13a and 13b in the region R11, respectively. Also with respect to the other terminals, the terminals having the same number but different subscripts "a" and "b" (terminals T12a and T12b, for example) form a pair and are electrically connected to the electrodes 13a and 13b in the region having the same number, among the regions R12 to R58, respectively, like the paired terminals T11a and T11b.

The ohmmeter M undergoes program control and measures and records values of resistance of the thin film layers 13 in the respective regions at predetermined intervals. Under the program control, the ohmmeter M not only detects a change in resistance of the thin film layer 13 in each region, but also determines whether or not the values of resistance of the thin film layers 13 in the respective regions are within a predetermined allowable range of uniformity. When determining that the resistance values of the thin film layers 13 in the respective regions are not uniform, the ohmmeter M determines in which region the resistance value of the thin film layer 13 is different from those in the other regions.

The method for examining the electrolyte membrane 10 using the ohmmeter M is specifically as follows: The detection membrane 11 is joined to the first surface 10a of the electrolyte membrane 10, and the electrolyte membrane 10 with the detection membrane 11 joined is arranged in a container 20 as in the first embodiment. Then, the detection membrane 11 is hydrogenated and kept in the hydrogenated state in the same manner as in the first embodiment. Then, with oxygen gas ($O_2$) being supplied to the first space 21, the ohmmeter M measures the resistance of the thin film layer 13 in each region.

If the electrolyte membrane 10 has no defects such as pin holes, oxygen gas supplied to the first space 21 is prevented from contacting the detection membrane 11 by the electrolyte membrane 10. Thus, the detection membrane 11 is not dehydrogenated and the resistance of the thin film layer 13 does not vary in any of the regions R11 to R58. In this case, the ohmmeter M determines that the electrolyte membrane 10 has no defect.

If, on the other hand, the electrolyte membrane 10 has a crack 10c in a region corresponding to the region R33 as shown in FIG. 4, for example, oxygen gas leaks from the second surface 10b side to the first surface side 10a of the electrolyte membrane 10 through the crack 10c. Consequently, under the catalytic action of the catalyst layer 12, the resistance of the thin film layer 13 in the region R33 near the crack 10c varies. At this time, finding that the resistance value in the region R33 is different from that in the other regions, the ohmmeter M determines that there exists a defect in the region corresponding to the region R33.

Also when a defect exists in a region other than the region corresponding to the region R33 or when more than one region have a defect, the ohmmeter M can identify such region(s) having a defect in the same way.

Next, as a method for examining an ion-conductive electrolyte membrane according to a third embodiment of the present invention, a method for examining an ion-conductive electrolyte membrane on oxygen ion conductivity will be described with reference to FIGS. 7 to 11.

Figure 7:
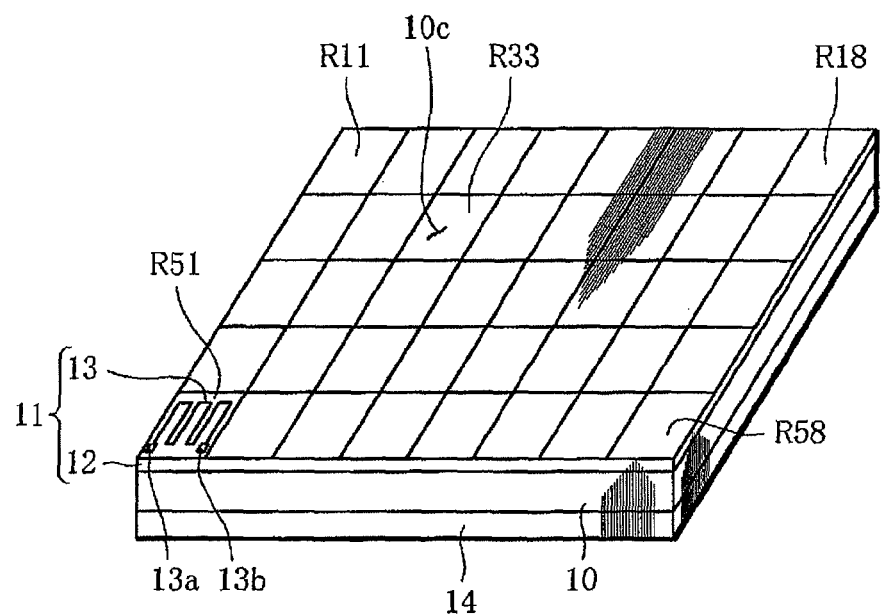
FIG. 7 is a perspective view showing an electrolyte membrane to be examined by an examination method according to a third embodiment of the present invention, with a detection membrane and an air electrode each joined to the electrolyte membrane.
Figure 8:
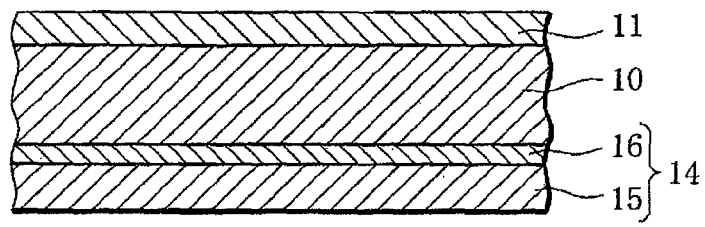
FIG. 8 is a schematic cross-sectional view showing the electrolyte membrane, detection membrane and air electrode of FIG. 7.
Figure 9:
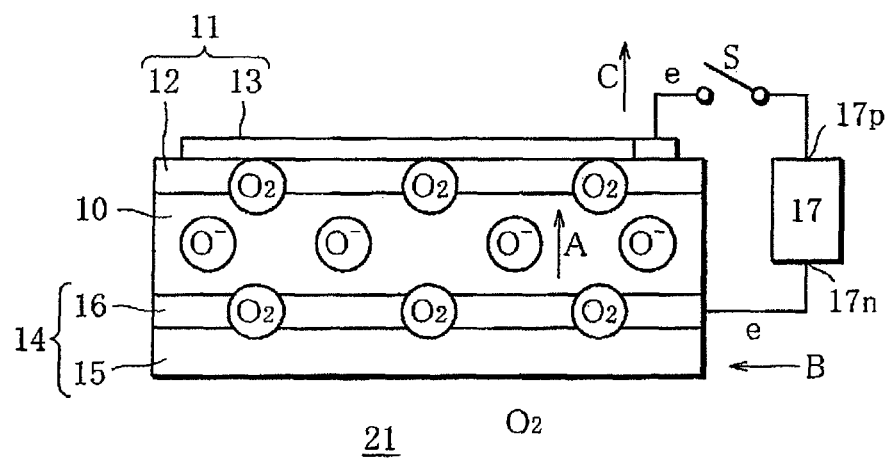
FIG. 9 is a schematic diagram showing a circuit structure for examining the electrolyte membrane on oxygen ion conductivity in one of regions R11 to R58 shown in FIG. 7, and also giving an explanation of oxygen ion conductivity of the electrolyte membrane.
Figure 10:
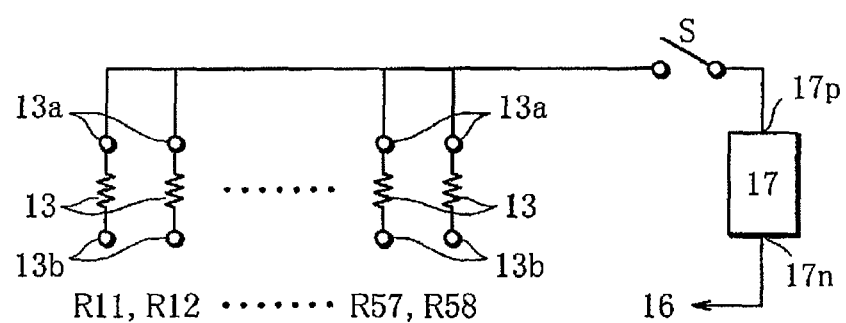
FIG. 10 is a diagram showing how the resistance of thin film layers is measured by the circuit of FIG. 9.
Figure 11:
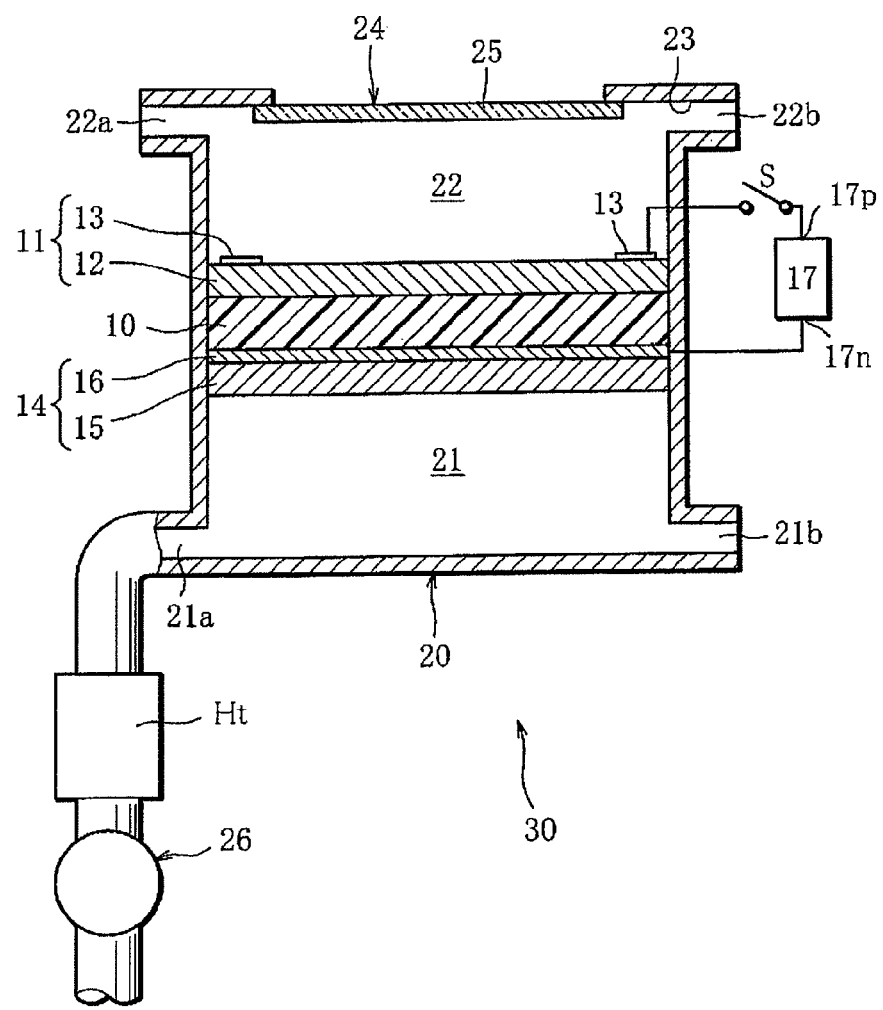
FIG. 11 is a schematic structural diagram showing an example of how an electrolyte membrane, etc. are arranged in a container in order to examine the electrolyte membrane on oxygen ion conductivity by the examination method according to the third embodiment of the present invention, and an examination apparatus according to a fourth embodiment of the present invention.

FIG. 7 is a perspective view showing an electrolyte membrane to be examined, with a detection membrane and an air electrode each joined to the electrolyte membrane. FIG. 8 is a schematic cross-sectional view showing the electrolyte membrane, air electrode and detection membrane. FIG. 9 is a schematic diagram showing an example of how a power supply circuit is connected between the air electrode and the detection membrane to examine the electrolyte membrane on oxygen ion conductivity, and also giving an explanation of the oxygen ion conductivity of the electrolyte membrane. FIG. 10 is a diagram showing how the resistance of thin film layers is measured by such circuit. FIG. 11 is a schematic diagram showing an example of how an electrolyte membrane, etc. are arranged in a container in order to examine the electrolyte membrane on oxygen ion conductivity by the examination method according to the third embodiment. The components similar in function to those in the above-described first and second embodiments will be assigned the same reference characters and the description thereof will be omitted.

As shown in FIG. 7, an electrolyte membrane 10 is divided into regions corresponding to regions R11 to R58 as in the above-described second embodiment. To a first surface 10a constituting one side of the electrolyte membrane 10, a detection membrane 11 equal in planar shape to the electrolyte membrane 10 is joined. For each of surface regions (regions R11 to R58) of the detection membrane 11 corresponding to the respective regions of the electrolyte membrane 10, a thin film layer 13 is formed with electrodes 13a, 13b, as in the second embodiment. As shown in FIGS. 7 and 8, an air electrode 14, equal in planar shape to the electrolyte membrane 10, comprises an oxygen diffusion membrane 15 and an cathode 16, where the cathode 16 is joined to a second surface 10b constituting the other side of the electrolyte membrane 10. Thus, the detection membrane 11 and the air electrode 14 face each other with the electrolyte membrane 10 interposed between them.

The oxygen diffusion membrane 15 of the oxygen electrode 14 is formed of carbon fibers, such as carbon cloth or carbon paper, or porous resin, porous ceramic, porous metal (foamed metal) or the like, for example. The thickness of the oxygen diffusion membrane 15 is 0.1 mm to 50 mm, for example. The anode 16 is a membrane formed of an oxygen ionization catalyst such as platinum, for example.

The air electrode 14 may be provided either as a component which constitutes, together with the electrolyte membrane 10, part of a membrane electrode assembly for a fuel cell, or as a member exclusively for examination which is temporarily joined to the electrolyte membrane 10 in examination.

As shown in FIG. 9, the cathode 16 of the air electrode 14 is connected to a negative terminal 17n of a power supply circuit 17, while the electrode 13a of the thin film layer 13 is connected to a positive terminal 17p of the power supply circuit 17 with a switch S interposed between them. Thus, the power supply circuit 17 constitutes part of an electric circuit passing electrons from the thin film layer 13 to the cathode 16, and can cause the thin film layer 13 to have a positive potential with respect to the cathode 16, thereby producing an electric field between the thin film layer 13 and the cathode 16.

In the examination of the electrolyte membrane 10 on oxygen ion conductivity, the electrolyte membrane 10 with the air electrode 14 and the detection membrane 11 joined is arranged in the container 20 as shown in FIG. 11. Then, the detection membrane 11 is hydrogenated and kept in the hydrogenated state in the same manner as in the above-described first embodiment. Then, to a first space 21 inside the container 20 facing the air electrode 14, oxygen gas ($O_2$) is supplied through a first supply port 21a. Naturally, both spaces are separated by the electrolyte membrane 10, etc. In FIG. 11, reference character 21b denotes a collection port for collecting unreacted oxygen gas, and reference character 22b denotes a gas discharge port for discharging an unreacted part of hydrogen gas supplied to hydrogenate the detection membrane 11, etc. It is preferable to keep the gas pressure in the first space 21 higher than the gas pressure in the second space 22 by a pump (gas pressure regulation means) 26. Such pressurizing by the pump 26 allows easier passage of oxygen gas through the air electrode 14.

Some time after the electrolyte membrane 10 starts to be heated by a heater, oxygen gas ($O_2$) ionizes at the air electrode, and the oxygen ions ($O^-$) produced start permeating through the electrolyte membrane 10. More specifically, oxygen gas ($O_2$) supplied to the first space 21 is diffused through the oxygen diffusion membrane 15 to reach the cathode 16 as shown in FIG. 9. If the switch S is in "ON" position at this time, the oxygen gas ($O_2$) gains electrons (e) supplied from the negative terminal 17n of the power supply circuit 17 to the cathode 16 to form oxygen ions ($O^-$). The oxygen ions ($O^-$) permeate through the electrolyte membrane 10 to reach the catalyst layer 12 of the detection membrane 11 as indicated by arrow A in the Figure, owing to electrical repulsive force generated by the negative potential of the power supply circuit 17 and electrical attractive force generated by the positive potential given to the thin film layer 13 with respect to the cathode 16. The oxygen ions ($O^-$) that have arrived at the catalyst layer 12 release electrons (e) to form oxygen gas ($O_2$) near the interface between the electrolyte membrane 10 and the catalyst layer 12. The oxygen gas ($O_2$) thus formed reacts with the thin film layer 13 under the action of the catalyst layer 12, or in other words, dehydrogenates the thin film layer 13. Here, the degree of dehydrogenation of the thin film layer 13 depends on the amount of oxygen ions ($O^-$) arriving at the detection membrane 11.

Incidentally, the switch S may be put into "ON" position either after or before oxygen gas ($O_2$) is supplied to the first space 21. To sum up, what is required is heating the electrolyte membrane 10 and putting the switch S into "ON" position so that oxygen ions ($O^-$) will permeate through the electrolyte membrane 10.

The heater heating the electrolyte membrane 10 may be either a heater heating the electrolyte membrane 10 by radiant heating, or a heater Ht heating the oxygen gas supplied to the first space 21 as shown in FIG. 11. The heating temperature obtained by the heater Ht is, for example so-called power generation start temperature for a fuel cell having the electrolyte membrane 10, which is approximately 300° C. to 1000° C., for example; It may, however, be lower than the power generation start temperature, as long as it allows the oxygen ions to start permeating through the electrolyte membrane 10.

If the oxygen ion conductivity of the electrolyte membrane 10 is uniform in the regions corresponding to the regions R11 to R58, the amount of oxygen ions ($O^-$) arriving at the catalyst layer 12 is equal in these regions. Thus, an ohmmeter M measures the resistance of the thin film layer 13 in each region, and determines whether or not the values of resistance of the thin film layers 13 in the respective regions are within a predetermined allowable range of uniformity. In this manner, it can be determined whether or not every region of the electrolyte membrane 10 has oxygen ion conductivity within a uniformity range allowable from the viewpoint of quality assurance, for example. If the oxygen ion conductivity of the electrolyte membrane 10 is not uniform, the resistance value of a thin film layer 13 in a region of the detection membrane 11 contacting a region of the electrolyte membrane having lower oxygen ion conductivity is different from the resistance value in the other regions. Thus, the ohmmeter M can not only determine whether or not the oxygen ion conductivity of the electrolyte membrane 10 is uniform, but also identify a region having lower oxygen ion conductivity.

The joining of the detection membrane 11 to the first surface 10a of the electrolyte membrane 10 does not need to create a perfectly tight contact leaving no space between them at all. This applies also to the joining of the air electrode 14 to the second surface 10b of the electrolyte membrane 10. The reason is that even if both or either of these connections includes a slight space, the electric field produced between the thin film layers 13 and the cathode 16 causes the oxygen ions ($O^-$) produced at the cathode 16 to permeate through the electrolyte membrane 10 and move straight to the detection membrane 11.

If the air electrode 14 constitutes part of a membrane electrode assembly for a fuel cell, together with the electrolyte membrane 10, the membrane electrode assembly with the air electrode 14 joined to the electrode membrane 14 can be subjected to the examination on oxygen ion conductivity.

The resistance of the thin film layers 13 in the regions R11 to R58 can be measured, with the electrode 13a of each thin film layer 13 connected to the positive terminal 17p of the power supply circuit 17 as shown in FIG. 10, for example. In other words, the ohmmeter M can measure the resistance of each thin film layer 13, while oxygen ions ($O^-$) are caused to be permeating through the electrolyte membrane 10 by the power supply circuit 17 connected. Here, the electrons (e) traveling through each thin film layer 13 produce a potential difference between the electrodes 13a and 13b of each thin film layer 13. If the oxygen ion conductivity is uniform in the regions corresponding to the regions R11 to R58, the potential difference between the electrodes 13a and 13b of the thin film layer is equal in these regions. Thus, the ohmmeter M can detect a difference in resistance in the thin film layers 13, on the basis of potential difference between the electrodes 13a and 13b of each thin film layer 13. Here, the shape of the electrolyte membrane is not restricted to a flat plane; it may be in another shape, as mentioned with respect to the first embodiment.

Next, as a method and apparatus for examining an ion-conductive electrolyte membrane according to a fourth embodiment of the present invention, an examination method and apparatus capable of conducting examination of an ion-conductive electrolyte membrane for defects and examination thereof on oxygen ion conductivity in a continuous process will be described with reference to the drawings referred to in the explanation of the above embodiments.

As shown in FIG. 11, an examination apparatus 30 according to this embodiment is similar in structure to the third embodiment, and examines an electrolyte membrane 10 as shown in FIGS. 7 and 8. Specifically, the examination apparatus 30 comprises a container 20, a power supply circuit 17, a heater Ht, a switch S and an ohmmeter M, as shown in FIGS. 9 to 11. Inside the container 20, a first space 21 (facing an air electrode) 21 and a second space 22 are separated by the electrolyte membrane 10. Heated by the heater Ht, the electrolyte membrane 10 comes to have oxygen ion conductivity.

With the switch S in "OFF" position, the examination apparatus 30 can examine the electrolyte membrane 10 for defects, by the procedure described with respect to the second embodiment. Further, with the switch S in "ON" position, it can examine the electrolyte membrane 10 on oxygen ion conductivity, by the procedure described with respect to the third embodiment.

Here, if a defect is detected in the defect examination of the electrolyte membrane 10 with the examination apparatus 30, it can be determined that the electrolyte membrane 10 does not have desired quality, without conducting examination on uniformity of oxygen ion conductivity. By conducting the above-described examination on uniformity of oxygen ion conductivity on those electrolyte membranes 10 which have passed the defect examination, electrolyte membranes 10 having no defect and being uniform in oxygen ion conductivity can be sorted out. It is to be noted that in this case, the electrolyte membranes determined to have no defect can be subjected to the examination on oxygen ion conductivity, without the need to newly hydrogenate the detection membrane.

In other words, the examination apparatus 30 can discover electrolyte membranes 10 not having desired quality in the preceding defect examination, and therefore save the examination on uniformity of oxygen ion conductivity for such defective electrolyte membranes 10. Thus, the examination apparatus 30 can not only shorten the examination time because of its continuous examination process, but also further shorten the examination time because it cuts the time consumed in wasteful examination. It goes without saying that also when the examination on uniformity of oxygen ion conductivity is conducted before the defect examination, the examination time can be reduced likewise. In this case, after the examination on oxygen ion conductivity, the detection membrane 11 needs to be newly hydrogenated. The examination apparatus 30 can thus simplify the process of examining the electrolyte membrane 10 and shorten the examination time.

The present invention is not restricted to the above-described embodiments, but can be modified appropriately without departing from the scope and spirit of the invention.

The invention claimed is:

1. A method for examining an ion-conductive electrolyte membrane, comprising the steps of:
    joining a detection membrane including a thin film layer to a first surface of the ion-conductive electrolyte membrane;
    supplying hydrogen gas to a space facing the first surface of the ion-conductive electrolyte membrane to hydrogenate the detection membrane;
    supplying oxygen gas to a space facing a second surface of the ion-conductive electrolyte membrane after the hydrogenation of the detection membrane;
    measuring electric resistance of the thin film layer; and
    determining if the ion-conductive electrolyte membrane has a defect based on whether a change in the electric resistance of the thin film is caused by dehydrogenation of the thin film layer due to oxygen gas leaking from the second surface to the first surface through the defect.

2. The method for examining the ion-conductive electrolyte membrane according to claim 1, wherein the thin film layer is provided for each of a plurality of regions into which the first surface of the ion-conductive electrolyte membrane is divided, and the step of determining if the ion-conductive electrolyte membrane has a defect includes a step of determining that a defect exists in a region corresponding to a thin film layer having a change in electric resistance.

3. The method for examining the ion-conductive electrolyte membrane according to claim 1, wherein gas pressure in the space facing the second surface of the ion-conductive electrolyte membrane is kept higher than gas pressure in a space facing the detection membrane.

4. The method for examining the ion-conductive electrolyte membrane according to claim 1, wherein the detection membrane includes the thin film layer and a catalyst layer brought in contact with the ion-conductive electrolyte membrane, and determining if the ion-conductive electrolyte membrane has a defect is determined by observing a change in electric resistance of the thin film layer, which arises when the ion-conductive electrolyte membrane has the defect and the thin film layer is dehydrogenated by oxygen gas passing through the defect under catalytic action of the catalyst layer.

5. The method for examining the ion-conductive electrolyte membrane according to claim 4, wherein the thin film layer is formed of a magnesium-nickel alloy, a magnesium-titanium alloy, a magnesium-niobium alloy, a magnesium-manganese alloy, a magnesium-cobalt alloy or magnesium, and the catalyst layer is formed of palladium or platinum.

6. A method for examining an ion-conductive electrolyte membrane, comprising the steps of:
    dividing a first surface of the ion-conductive electrolyte membrane into a plurality of regions;
    joining a detection membrane having thin film layers provided to correspond to the regions, respectively, to the first surface of the ion-conductive electrolyte membrane;
    joining an air electrode to a second surface of the ion-conductive electrolyte membrane;
    supplying hydrogen gas to a space facing the detection membrane to hydrogenate the detection membrane;
    connecting an electric circuit between the thin film layers and the air electrode for each of the regions; heating the ion-conductive electrolyte membrane to have oxygen ion conductivity;
    supplying oxygen gas to a space facing the air electrode to ionize at the air electrode; supplying oxygen ions resulting from the ionization from the air electrode to the ion conductive electrolyte membrane to permeate through the ion conductive electrolyte membrane;
    detecting electric resistance of the thin film layer dehydrogenated by the oxygen ions permeating through the ion-conductive electrolyte membrane for each of the regions; and
    determining if the ion-conductive electrolyte membrane has uniform oxygen ion conductivity, depending on whether the electric resistances of the thin film layers, detected for each of the regions, are uniform.

7. The method for examining the ion-conductive electrolyte membrane according to claim 6, wherein the electric circuit is a power supply circuit, and a negative terminal of the power supply circuit is electrically connected to the air electrode while a positive terminal of the power supply circuit is electrically connected to the thin film layers.

8. The method for examining the ion-conductive electrolyte membrane according to claim 7, wherein the air electrode includes an oxygen diffusion membrane and a cathode, and the cathode is electrically connected to the negative terminal of the power supply circuit and brought in contact with the ion-conductive electrolyte membrane.

9. The method for examining the ion-conductive electrolyte membrane according to claim 7, wherein the detection membrane includes the thin film layers and a catalyst layer brought in contact with the ion-conductive electrolyte membrane, and the step of detecting electric resistance of the thin film layer for each of the regions includes a step of detecting a change in electric resistance of the thin film layer for each of the regions, which results from dehydrogenation of the corresponding thin film layer under catalytic action of the catalyst layer by oxygen ions permeating through the ion-conductive electrolyte membrane.

10. The method for examining the ion-conductive electrolyte membrane according to claim 9, wherein the thin film layers are each formed of a magnesium-nickel alloy, a magnesium-titanium alloy, a magnesium-niobium alloy, a magnesium-manganese alloy, a magnesium-cobalt alloy or magnesium, and the catalyst layer is formed of palladium or platinum.

11. An apparatus for examining an oxygen ion-conductive electrolyte membrane, comprising a detection membrane having a plurality of thin film layers and joined to a first surface of the oxygen ion-conductive electrolyte membrane, and an air electrode joined to a second surface of the oxygen ion-conductive electrolyte membrane, the apparatus further comprising:
    a container which provides a space facing the air electrode and a space facing the detection membrane;
    an electric circuit which is selectively connected between the air electrode and each of the thin film layers arranged to correspond to a plurality of regions into which the first surface of the ion-conductive electrolyte membrane is divided, with a switch interposed between;
    a heater for heating the ion-conductive electrolyte membrane, thereby causing the ion-conductive electrolyte membrane to have oxygen ion conductivity; and
    an ohmmeter for measuring electric resistance of each of the thin film layers,
    wherein the apparatus examines if the ion-conductive electrolyte membrane has a defect by:
    supplying hydrogen gas to the space facing the detection membrane to hydrogenate the detection membrane;
    supplying oxygen gas to the space facing the air electrode after the hydrogenation of the detection membrane, with the switch in "OFF" position;

measuring electric resistance of each of the thin film layers by the ohmmeter; and examining if a change in the measured electric resistance of each thin film layer occurs, and wherein the apparatus examines if the ion-conductive electrolyte membrane has uniform oxygen ion conductivity by:

heating the ion-conductive electrolyte membrane by the heater to cause the ion-conductive electrolyte membrane to have oxygen ion conductivity;

supplying oxygen gas to the space facing the oxygen electrode, with the switch in "ON" position;

measuring electric resistance of each of the thin film layers by the ohmmeter; and examining whether the electric resistances detected for each of the thin film layers are uniform.

12. The apparatus for examining the ion-conductive electrolyte membrane according to claim 11, wherein the electric circuit is a power supply circuit, and a negative terminal of the power supply circuit is electrically connected to the air electrode while a positive terminal of the power supply circuit is electrically connected to the thin film layers.

13. The apparatus for examining the ion-conductive electrolyte membrane according to claim 11, further comprising the apparatus further comprises a gas pressure regulation means for keeping gas pressure in the space facing the air electrode higher than gas pressure in the space facing the detection membrane.

* * * * *